United States Patent
Odom et al.

(10) Patent No.: US 10,103,402 B2
(45) Date of Patent: Oct. 16, 2018

(54) LIQUID PHENOTHIAZINE CATHOLYTES FOR NON-AQUEOUS REDOX FLOW BATTERIES

(71) Applicant: University of Kentucky Research Foundation, Lexington, KY (US)

(72) Inventors: Susan A. Odom, Lexington, KY (US); Matthew D. Casselman, Riverside, CA (US); Aman Preet Kaur, Lexington, KY (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 0 days.

(21) Appl. No.: 15/366,610

(22) Filed: Dec. 1, 2016

(65) Prior Publication Data

US 2017/0155164 A1    Jun. 1, 2017

Related U.S. Application Data

(60) Provisional application No. 62/261,370, filed on Dec. 1, 2015.

(51) Int. Cl.
- *H01M 8/22* (2006.01)
- *H01M 8/18* (2006.01)
- *C07D 279/22* (2006.01)

(52) U.S. Cl.
CPC .......... *H01M 8/222* (2013.01); *C07D 279/22* (2013.01); *H01M 8/188* (2013.01); *H01M 2300/0025* (2013.01)

(58) Field of Classification Search
None
See application file for complete search history.

(56) References Cited

U.S. PATENT DOCUMENTS

| | | | |
|---|---|---|---|
| 3,803,140 A * | 4/1974 | Cook | C09K 15/30 252/402 |
| 4,397,922 A | 8/1983 | Pokhodenko et al. | |
| 7,615,312 B2 | 11/2009 | Dahn et al. | |
| 8,247,680 B2 | 8/2012 | Inagaki et al. | |
| 9,178,254 B2 | 11/2015 | Lee et al. | |
| 9,203,080 B2 | 12/2015 | Deronzier et al. | |
| 9,300,000 B2 | 3/2016 | Jansen et al. | |
| 2006/0217433 A1 * | 9/2006 | Conner | A61K 31/00 514/418 |
| 2012/0028137 A1 | 2/2012 | Chase et al. | |
| 2014/0072843 A1 | 3/2014 | Liemersdorf et al. | |
| 2014/0178735 A1 | 6/2014 | Wang et al. | |
| 2014/0288060 A1 * | 9/2014 | Krappmann | A61K 31/5415 514/225.5 |
| 2015/0372333 A1 * | 12/2015 | Odom | H01M 8/188 429/108 |
| 2017/0062842 A1 * | 3/2017 | Huang | C07D 279/22 |
| 2018/0006336 A1 * | 1/2018 | Odom | H01M 8/188 |
| 2018/0026297 A1 * | 1/2018 | Odom | H01M 8/188 429/340 |
| 2018/0057471 A1 * | 3/2018 | Odom | C08G 65/3348 |

OTHER PUBLICATIONS

Milshtein et al ("High Current Density, Long Duration Cycling of Soluble Organic Active Species for Non-aqueous Redox Flow Batteries", Energy & Environmental Science, Issue 11, (2016), p. 3531-3543).*

Hart et al ("Phenothiazine-Sensitized Organic Solar Cells: Effect of Dye Anchor Group Positioning on the Cell Performance", ACS Applied Materials & Interfaces (2012), vol. 4(11), p. 5813-5820) (Year: 2012).*

* cited by examiner

*Primary Examiner* — Sin J Lee
(74) *Attorney, Agent, or Firm* — King & Schickli, PLLC

(57) ABSTRACT

Highly soluble, liquid phenothiazines containing methoxy-terminated ether and oligoether substituents are disclosed with high diffusion coefficients and robust performance in electrochemical measurements, which can be synthesized in one step from commercially-available starting materials, thereby circumventing previous synthetic limitations.

5 Claims, 12 Drawing Sheets

# LIQUID PHENOTHIAZINE CATHOLYTES FOR NON-AQUEOUS REDOX FLOW BATTERIES

RELATED APPLICATIONS

This application claims priority to U.S. Provisional application 62/261,370, filed Dec. 1, 2015, the full disclosure of which is herein incorporated by reference.

FIELD OF THE INVENTION

This document relates generally to new compositions for catholytes in a redox flow battery systems, as well as redox flow batteries with phenothiazine derivative catholyte solutions.

BACKGROUND

To increase reliance on renewable energy supplies such as solar and wind power, it is necessary to increase the amount of energy storage systems connected to the electrical grid. Of the electrochemical energy storage (EES) systems under consideration for stationary storage, redox flow batteries (RFBs) are of immense interest (Weber et al., *J. Appl. Electrochem.*, 2011, 41, 1137-1164; Leung et al., *RSC Advances*, 2012, 2, 10125-10156; Parasuraman et al., *Electrochim. Acta*, 2013, 101, 27-40; Shin et al., *RSC Advances*, 2013, 3, 9095-9116; Wang et al., *Adv. Fun. Mater.*, 2013, 23, 970-986; Alotto et al., *Renewable and Sustainable Energy Reviews*, 2014, 29, 325-335). Aqueous-based RFBs containing vanadium complexes have been commercialized on scales as large as 5 MW ("Rongke Power 5 MW/10 MWh VFB Energy Storage System successfully finish power transmission to Liaoning Power Grid," www.rongkepower.com/index.php?s=/article/show/id/140/language/en, Accessed Jul. 20, 2015). Through the replacement of aqueous components, which limit charging potentials to 1.5 V due to the working electrochemical window of water, with organic materials, it may be possible to develop batteries with charging voltages as high as 5 V.

Despite decades of research on the use of organometallic compounds as electro-active materials in non-aqueous RFBs, most systems have been limited by low solubility, poor capacity retention, and/or low faradaic efficiency (Soloveichik, *Chem. Rev.*, 2015, ASAP article). Few examples of highly soluble species have been reported, and even in these cases, testing has been limited to concentrations too low for practical use in commercial applications (Cappillino et al., *Adv. Energy Mater.*, 2014, 4; Cabrera et al., *J. Phys. Chem. C*, 2015; Suttil et al., *J. Mater. Chem. A*, 2015, 3, 7929-7938; Hwang et al., *Chem Sus Chem*, 2015, 8, 310-314). More recently, reports of non-aqueous RFBs containing organic electro-active materials have surfaced. N-oxidanyl amines (e.g. TEMPO), dialkoxybenzenes, and phenothiazines serve as electron-donating electro-active materials, while phthalimide, anthroquinones, quinoxilanes, fluorenone, and viologen act as electron-accepting counterparts (Li et al., *Electrochem. Solid-State Lett.*, 2011, 14, A171-A173; Wei et al., *Adv. Mater.*, 2014, 26, 7649-7653; Wei et al., *Angew. Chem. Int. Ed.*, 2015, 54, 8684-8687; Brushett et al., *Adv. Energy Mater.*, 2012, 2, 1390-1396; Kaur et al., *Energy Tech.*, 2015, 3, 476-480; Wang et al., *Chem. Commun.*, 2012, 48, 6669-6671; Nagarjuna et al., *J. Am. Chem. Soc.*, 2014, 136, 16309-16316). Many of the electron donors have been used as electron-transfer catalysts in other energy storage and collection applications, including redox shuttles for overcharge protection of lithium-ion batteries (LIBs), electron-transfer agents in lithium-air batteries,[27,28] and redox mediators in dye-sensitized solar cells, among others (Chen et al., *Electrochim. Acta*, 2009, 54, 5605-5613; Balakrishnan et al., *J. Power Sources*, 2006, 155, 401-414; Buhrmester et al., *J. Electrochem. Soc.*, 2006, 153, A288-A294; Ergun et al., *J. Phys. Chem. C*, 2014, 118, 14824-14832; Ergun et al., *Chem. Commun.*, 2014, 50, 5339-5341; Kaur et al., *J. Mater. Chem. A*, 2014, 2, 18190-18193; Narayana et al., *Chem Phys Chem*, 2015, 16, 1179-1189; Chen et al., *Nat. Chem.*, 2013, 5, 489-494; Lacey et al., *Electrochem. Commun.*, 2013, 26, 74-76; Hamann et al., *Energy Environ. Sci.*, 2011, 4, 370-381).

N-ethylphenothiazine (EPT, FIG. 1) is a particularly stable electron-donating compound that oxidizes at ca. 3.5 V vs. $Li^{+/0}$ in carbonate-based electrolytes. This commercially available material survives extensive overcharge cycling in LIBs. Studies of EPT show that it is stable in aprotic, organic solvents in the neutral and the singly oxidized (radical cation) states (Odom et al., *Energy Environ. Sci.*, 2014, 7, 760-767). It was considered whether these characteristics could allow EPT to serve as an effective electro-active material in non-aqueous RFBs as a one-electron donor. However, EPT's limited solubility in organic solvents (ca. 0.1 M) makes it impractical for this application, which requires electro-active material concentrations of 1 to 2 M to be competitive with the capacities of aqueous RFBs. In comparison, it was reported that the EPT derivative 3,7-bis(trifluoromethyl)-N-ethylphenothiazine (BCF3EPT) dissolves at concentrations as high as 1.5 to 2 M in organic solvents and electrolytes and is even more stable than EPT (Odom et al., *MRS Online Proceedings Library*, 2015, 1740, DOI: 10.1557/opl.2015.1204; Kaur et al., *J. Electrochem. Soc.*, 2015, manuscript accepted for publication). However, its synthesis requires three steps, the third of which is low yielding. Focusing studies on easily-scalable materials, research was therefore targeted to produce products that could be prepared in a single step from commercially available components.

Phenothiazines are generally stable, electron-donating electro-active materials with potential use in energy collection and storage applications and in electrochemically mediated synthesis. To be practical as electron-donating electro-active catholytes for non-aqueous redox flow batteries, solutions of high capacity are required. The present invention described herein provides highly soluble, liquid phenothiazines containing methoxy-terminated ether and oligoether substituents with high diffusion coefficients and robust performance in electrochemical measurements. Further, the catholyte solutions described herein can be synthesized in one step from commercially-available starting materials, thereby circumventing previous synthetic limitations.

SUMMARY OF THE INVENTION

The present invention provides for a composition for a catholyte solution comprising a phenothiazine derivative with a substituent at the N position. In some embodiments, the substituent may be either an oligoether or a methoxy-terminated ether. In other embodiments, the substituent is an oligoether or an oligoglycol chain, which may be branched or linear. Examples of branched derivatives include the following structures:

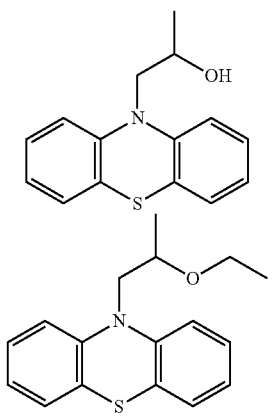

The catholyte compositions may further comprise at least a second substituent at the 1, 2, 3, 4, 6, 7, 8 and/or 9 positions. These substituents may be a halogen, an alkoxy group, a carbonyl group, a nitrile group, a nitro group, an alkyl, a perfluoroalkyl or combinations thereof.

In certain embodiments, the phenothiazine derivative is either N-(2-methoxyethyl)phenothiazine (MEPT) and/or N-[2-(2-methoxyethoxy)ethyl]phenothiazine (MEEPT). These derivative have the following structures:

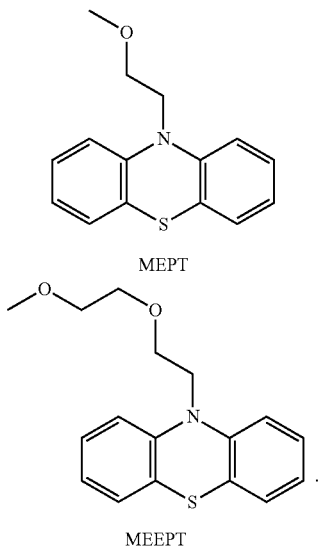

The present invention also provides for a catholyte solution for a flow battery comprising the catholyte composition described herein and an organic solvent, such as a lithium solvent.

The present invention further provides for a flow battery comprising a positive electrode resting in the catholyte solutions described herein and a negative electrode. The negative electrode and the positive electrode may be separated by a membrane.

The present invention also provides for methods of producing a phenothiazine derivative with a substituent at the N position. These methods may include the steps of deprotonation of phenothiazine and a subsequent $S_N2$ reaction with a corresponding alkyl halide, thereby yielding the phenothiazine derivative. In certain embodiments, the alkyl halide is 2-chloroethyl methyl ether or 1-bromo-2-(2-methoxyetoxy) ethane.

DETAILED DESCRIPTION

Figure 1:
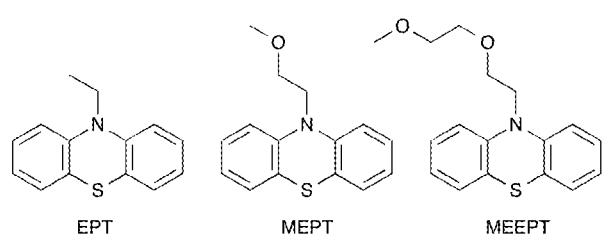
FIG. 1 shows the chemical structures of N-ethylphenothiazine (EPT), N-(2-methoxyethyl)phenothiazine (MEPT), and N-(2-(2-methoxyethoxy)ethyl)phenothiazine (MEEPT).

The present invention provides for two new phenothiazine-based electro-active materials, as well as derivatives thereof. The compounds may be prepared in one step from commercially available phenothiazine. The two newly identified compounds comprise N-(2-methoxyethyl)phenothiazine (MEPT) and N-[2-(2-methoxyethoxy)ethyl]phenothiazine (MEEPT) (see, e.g., FIG. 1). The products contain methoxy-terminated ether or oligoether substituents, which provide greater polarities relative to simple alkyl groups. These compounds are liquids at room temperature and are highly soluble in organic electrolytes. Their performance in cyclic voltammetry and overcharge experiments suggests that they are good candidates for catholytes in non-aqueous RFBs. The structure of each is as follows:

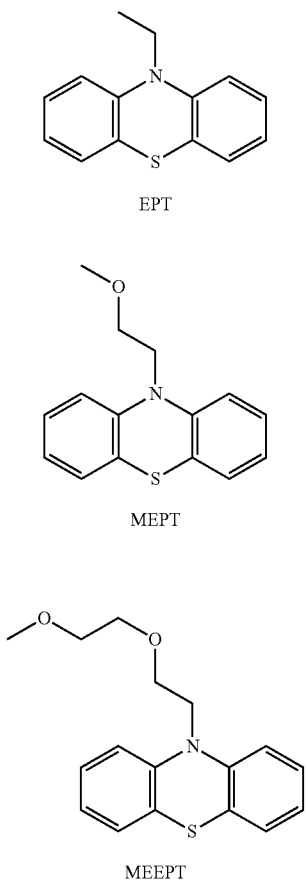 [SMILES: CCN1c2ccccc2Sc2ccccc21 ; COCCN1c2ccccc2Sc2ccccc21 ; COCCOCCN1c2ccccc2Sc2ccccc21]

EPT

MEPT

MEEPT

Other new and useful phenothiazine-based electro-active materials include MEPT and MEEPT with longer oligoglycol chains at the N position of the phenothiazine ring system, both linear and branched. Other compounds include substituents at the 1, 2, 3, 4, 6, 7, 8 and/or 9 positions selected from a group including, but not limited to, halogen, alkoxy group, carbonyl, nitrile, nitro, alkyl and perfluoroalbyl. Further, some salts that are used as electrolytes may be dissolved in the compound MEEPT, including LiTFSI. Examples of other derivatives include the following structures:

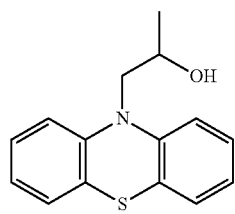 [SMILES: CC(O)CN1c2ccccc2Sc2ccccc21]

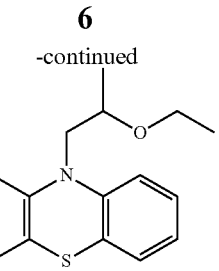

The compounds of the present invention have demonstrated effective use as a catholyte in a flow battery system.

The compounds of the present invention can be prepared by deprotonation of phenothiazine and a subsequent $S_N2$ reaction with a corresponding alkyl halide. This process has produced MEPT and MEEPT in good yields. The compounds were isolated as colorless oils that were miscible with a variety of organic solvents. Both derivatives were miscible up to 50 wt. % in the common battery electrolyte, 1.2 M LiPF$_6$ in ethylene carbonate/ethyl methyl carbonate (EC/EMC, 3:7 wt. ratio) (Table 1), which corresponds to a concentration of ca. 2 M. In contrast, the solubility of EPT is limited to 0.1 M in the same electrolyte. Notably, MEPT and MEEPT are less expensive to produce than other soluble electron-donating materials; compared to the recently-reported liquid electro-active material 1,4-di(tert-butyl)-2-methoxy-5-(2-methoxyethoxy)benzene (ANL RS-8), which is synthesized from 2,5-di(tert-butyl)-4-methoxyphenol, phenothiazine—the immediate precursor to MEPT and MEEPT—is more than 100 times less expensive (Huang et al., *Adv. Energy Mater.*, 2015, 5, DOI:10.1002/aenm.201401782).†

Figure 2:
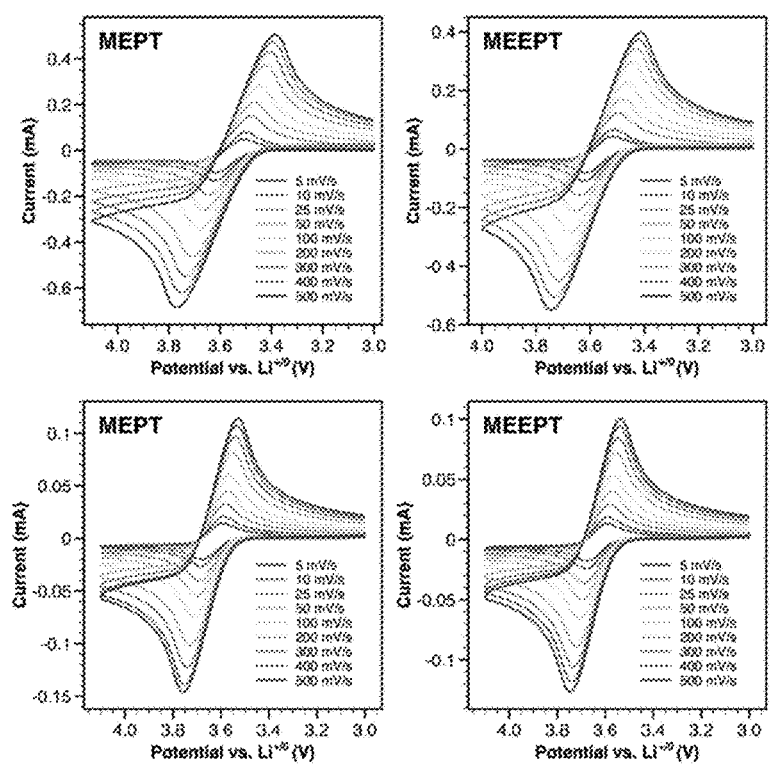
FIG. 2 shows cyclic voltammograms of MEPT (top left) and MEEPT (top right) at 80 mM in 1.2 M $LiPF_6$ in EC/EMC (3:7 wt. ratio) recorded at scan rates from 5 to 500 mV/s; MEPT (bottom left) and MEEPT (bottom right) at 10 mM in 0.5 M $LiBF_4$ in PC recorded at scan rates from 5 to 500 mV/s.
Figure 7:
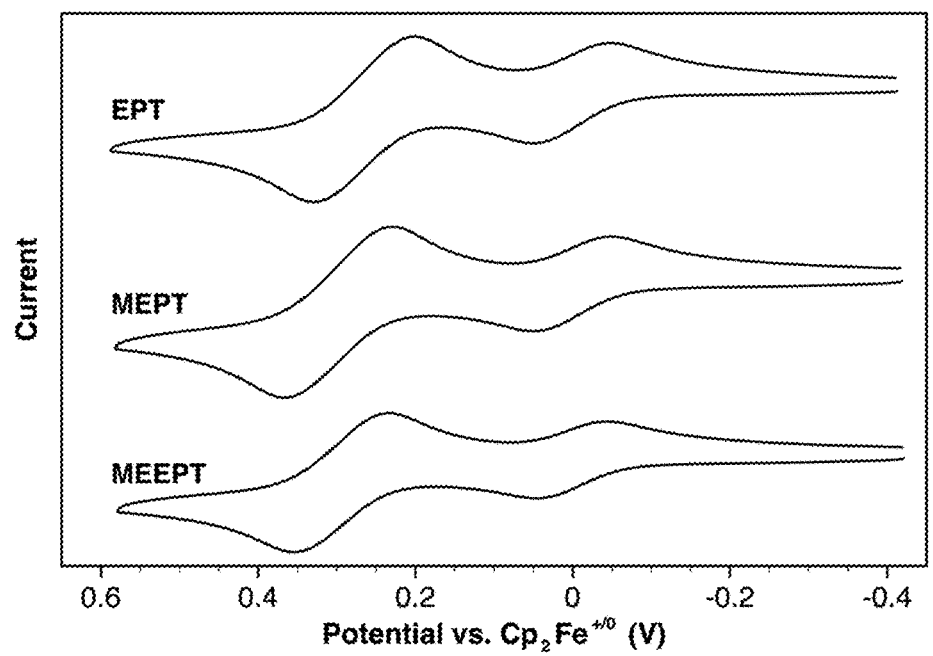
FIG. 7 shows cyclic voltammograms of EPT, MEPT and MEEPT at 0.8 mM in DCM (100 mM $TBA-PF_6$ supporting electrolyte) vs. $Cp_2Fe^{+/0}$ at 0 V, shown with ferrocene as an internal standard at 0 V, recorded at a scan rate of 100 mV/s
Figure 8:
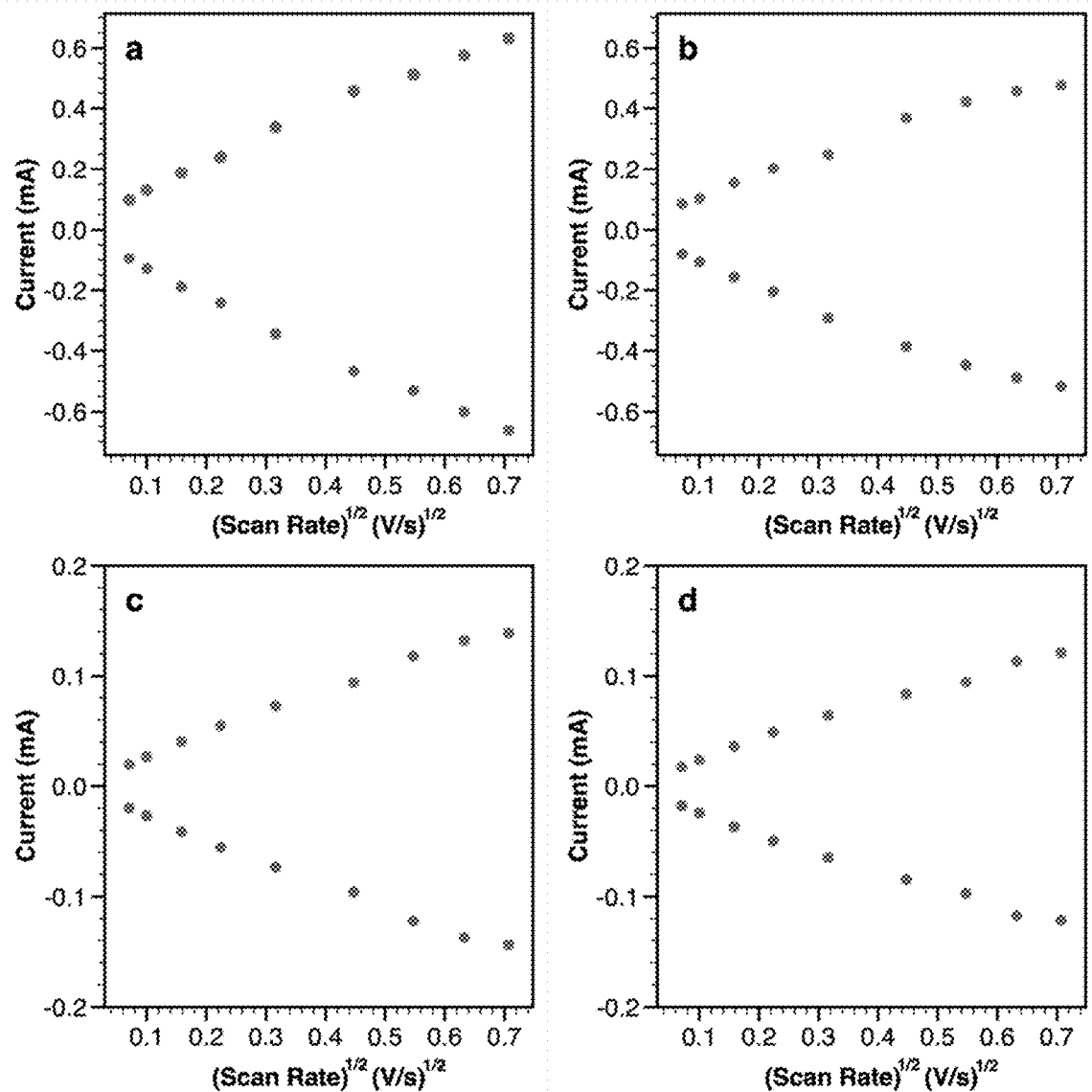
FIG. 8 shows plots of peak current vs. square root of scan rate of 80 mM MEPT (a) and 80 mM MEEPT (b) in 1.2 M $LiPF_6$ in EC/EMC (3:7 wt. ratio); 10 mM MEPT (c) and 10 mM MEEPT (d) in 0.5 M $LiBF_4$ in PC
Figure 9:
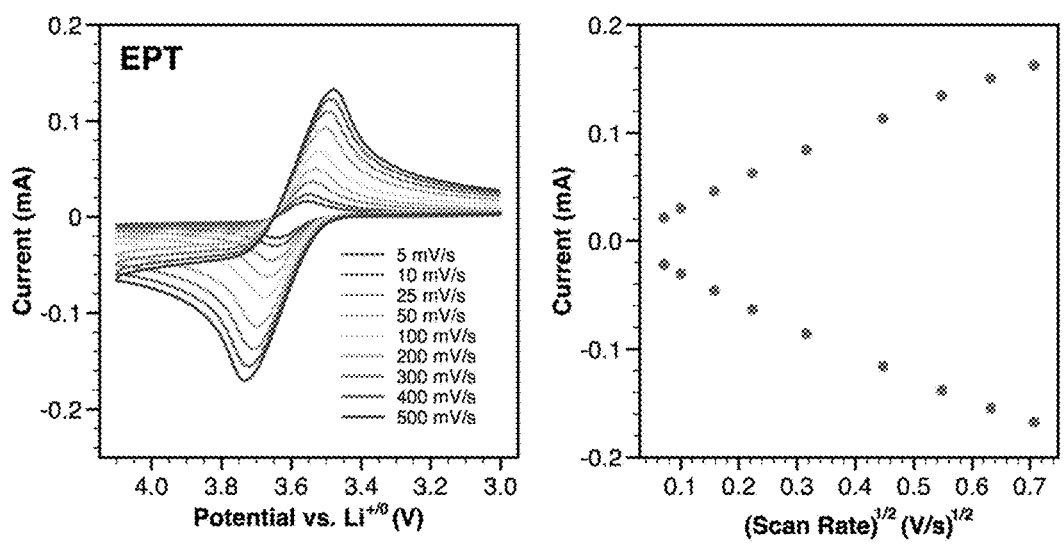
FIG. 9 shows: Left: Cyclic voltammograms of EPT at 10 mM in 0.5 M $LiBF_4$ in PC recorded at scan rates from 5 to 500 mV/s. Right: Plot of peak current vs. square root of scan rate of 80 mM EPT in 0.5 M $LiBF_4$ in PC.

The compounds of the present invention provide for components of a redox flow battery system, particularly as part of a catholyte composition. The studies described herein detail their effectiveness for such. The position and reversibility of redox events was determined by cyclic voltammetry (CV), performed in dichloromethane (DCM) containing 0.1 M tetra(n-butyl)ammonium hexafluorophosphate (TBA-PF$_6$) (FIG. 7), in EC/EMC (3:7) containing 1.2 M LiPF$_6$ (FIG. 2), or in propylene carbonate (PC) containing 0.5 M LiBF$_4$ (FIG. 2). Both compounds show reversible first oxidations in all electrolytes. In TBA-PF$_6$/DCM, MEPT ($E_{1/2}^{+/0}$=0.30 V vs. Cp$_2$Fe$^{+/0}$) and MEEPT ($E_{1/2}^{+/0}$=0.29 V vs. Cp$_2$Fe$^{+/0}$) oxidize at 0.03 and 0.02 V higher, respectively, than EPT (Table 1). In contrast, though the oxidation potentials of the new compounds were still higher than that of EPT in LiPF$_6$/EC/EMC, a larger difference was observed: MEPT ($E_{1/2}^{+/0}$=3.56 V vs. Li$^{+/0}$) and MEEPT ($E_{1/2}^{+/0}$=3.60 V vs. Li$^{+/0}$) oxidized at 0.06 and 0.09 V higher, respectively, than EPT (Table 1). The increase in oxidation potential in the lithium-based electrolytes can be attributed to the coordination, through the oligoether side chain, of MEPT to Li$^+$, a characteristic that is even more pronounced in the case of MEEPT.

Figure 11:
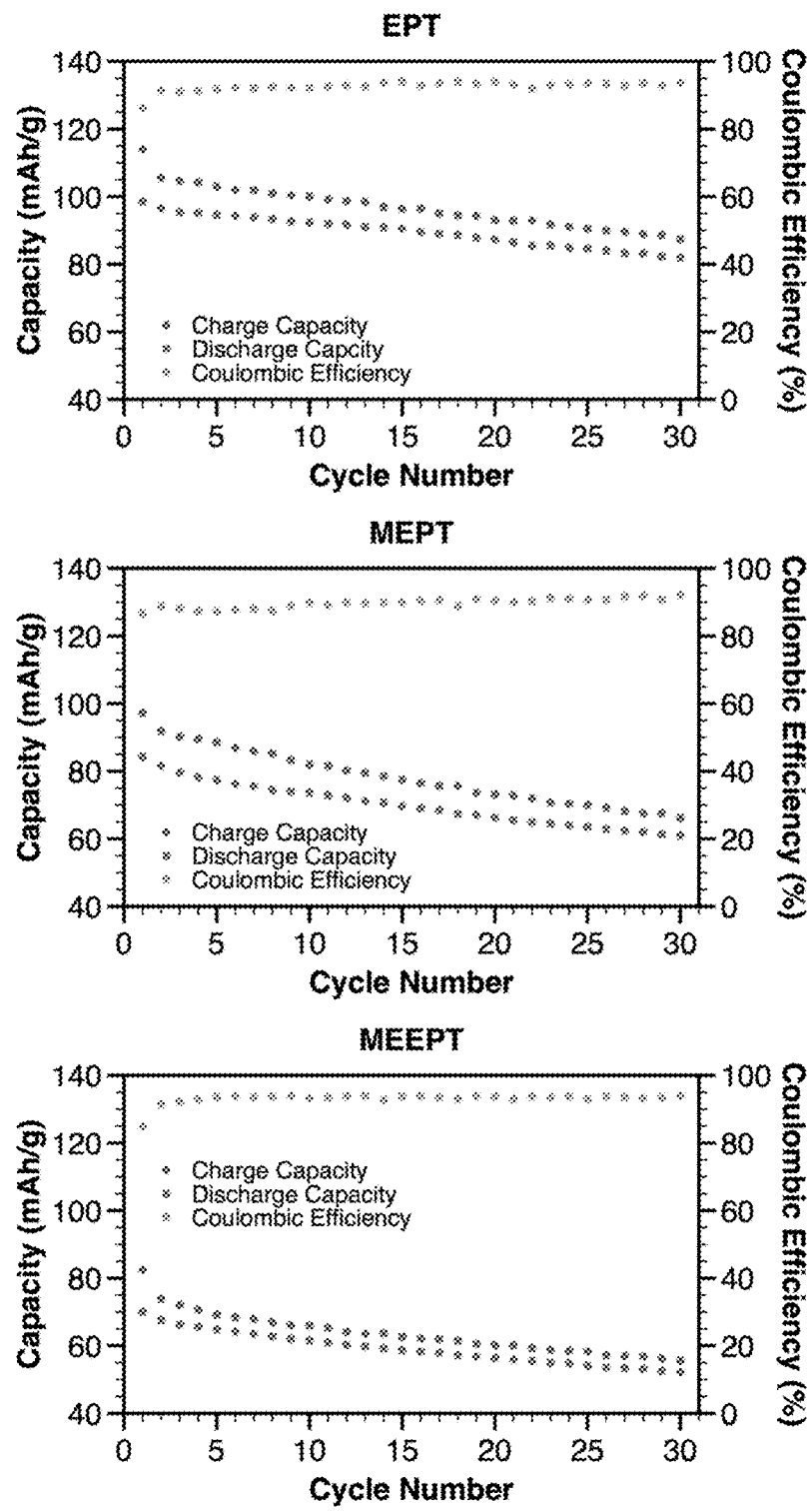
FIG. 11 shows profiles of capacity and corresponding coulombic efficiency vs. cycle number for EPT, MEPT and MEEPT at 10 mM in 0.5 M $LiBF_4$ in PC from 0-100% SOC at a rate of C/5 for 120 h in a coin cell with Li metal as the negative electrode
Figure 12:
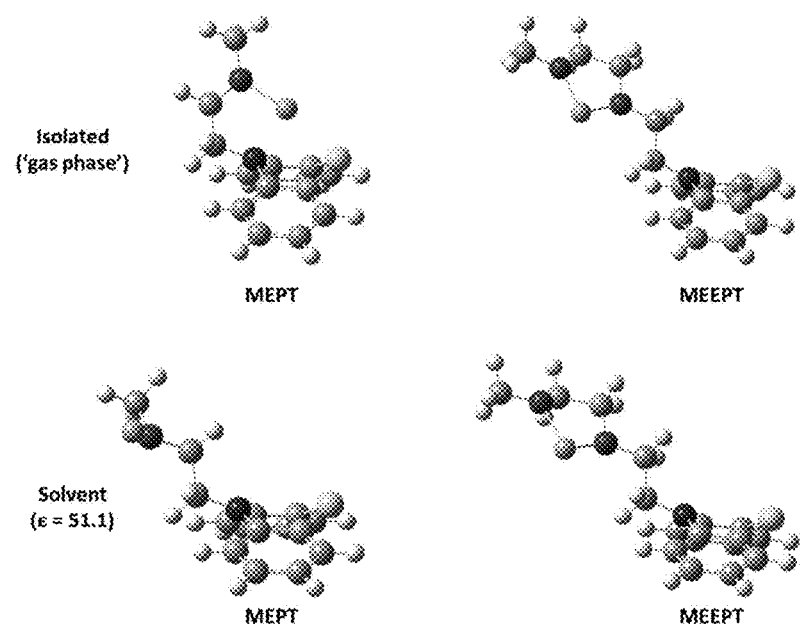
FIG. 12 shows geometry minimized configurations of MEPT and MEEPT with chelated $Li^+$. All calculations were performed at the B3LYP/6-311G(d,p) level of theory, and the SCRF polarizable continuum model with $\varepsilon=51.1$ was used to account for the battery environment

To confirm this hypothesis, a density functional theory (DFT) investigation of MEPT and MEEPT was performed to explore the potential for the methoxyethyl and methoxyethoxyethyl groups to bind Li$^+$, and the resulting influence on the adiabatic ionization potentials (IPs). The hybrid B3LYP density functional was used in conjunction with the 6-311G(d,p) basis set to optimize both the neutral and radical-cation states of EPT, MEPT, and MEEPT, and the ground state of Li$^+$; this level of theory has been previously shown to produce good results concerning the geometries and ionization potentials of phenothiazines (Casselman et al., *Phys. Chem. Chem. Phys.*, 2015, 17, 6905-6912). An implicit solvent dielectric was employed through the use of the default self-consistent reaction field (SCRF) polarizable continuum method in Gaussian09 (revision A.02); a dielectric constant, ε, of 51.1 (formic acid) was used to represent the EC/EMC electrolyte environment (Tomasi et al., *Chem. Rev.*, 2005, 105, 2999-3094; Frisch, *Gaussian 09, Revision A.02*, 2009). As shown in Table 2 and FIGS. 11 and 12, inclusion of the solvent environment plays a considerable role in the minimized geometries, and resulting electronic properties, of the $Li^+$-chelated species. All geometries were confirmed to be minima on the potential energy landscape through normal mode analysis, and all energies reported take into account the zero-point energy correction. The results are summarized in Table 1 (the AIP for EPT reported varies slightly to previous reports, see Kaur et al., *J. Mater. Chem. A*, 2014, 2, 18190-18193 and Huang et al., *Adv. Energy Mater.*, 2015, 5, DOI:10.1002/aenm.201401782, due to the current inclusion of the continuum dielectric model to account for the electrolyte environment and accounting for the zero-point energy correction).

The two ether moieties in the methoxyethoxyethyl group (MEEPT) appended to phenothiazine lead to a stronger chelation of $Li^+$ when compared to the methoxyethyl group (MEPT), both in the neutral (binding energy, BE, 10.0 kcal/mol MEEPT vs. 3.9 kcal/mol MEPT) and radical-cation states (7.9 kcal/mol MEEPT vs 1.5 kcal/mol MEPT). For the neutral species, the presence of the $Li^+$ energetically stabilizes the highest-occupied molecular orbitals (HOMOs) by 0.1 eV through polarization effects; this effect is fairly significant given that a solvent dielectric is taken into account in the DFT calculations, as the dielectric can act to shield the phenothiazine moiety from the $Li^+$. In turn, in agreement with the CV results, the bound $Li^+$ increases the phenothiazine IP by about 0.1 eV when compared to the non-$Li^+$-containing systems. While the 0.04 V, or less, difference in MEPT and MEEPT oxidation potential shown experimentally is not fully reproduced, the DFT calculations reveal that the $Li^+$ stabilizes the phenothiazine cation.

MEPT and MEEPT were subjected to CV experiments at variable scan rates in the carbonate-based electrolytes and DCM to determine their diffusion coefficients (FIG. 2, 8). At 80 mM, MEPT and MEEPT diffuse more slowly than EPT. This observation can be explained by the interaction of MEPT and MEEPT with a lithium ion from the electrolyte, which increases the size/molecular weight of the shuttle. Because the additional oxygen in MEEPT enhances the ability for $Li^+$ chelation, this effect is posited to be responsible for the further reduction in its diffusion rate.

Although MEPT and MEEPT reversibly oxidize in CV experiments, this experiment does not predict long-term stability, which is important for RFBs. The stability of the radical cation—typically the more reactive form of the electro-active material—can be monitored using UV-vis absorption spectroscopy as these species absorb light in the visible region. This method has proven to be useful for the evaluation of redox shuttle candidates for overcharge protection in LIBs, another application in which the radical cation is involved in electron transfer. The stability of the EPT, MEPT, and MEEPT radical cations were compared in dilute dichloromethane solutions after generation through chemical oxidation with tris(4-bromophenyl)aminium hexachloroantimonate ($TBPA-SbCl_6$). The absorption spectra of the three solutions display nearly identical features and remain almost unchanged for the 5 h during which the

TABLE 1

Calculated adiabatic ionization potentials (IPs), half-wave oxidation potentials ($E_{1/2}^{+/0}$), diffusion coefficients, and solubilities of EPT, MEPT, and MEEPT.

| Compound | Calculated adiabatic IP of molecule (eV) | Calculated adiabatic IP with $Li^+$ (eV) | $E_{1/2}^{+/0}$ vs. $Cp_2Fe^{+/0}$ (V) in TBA-$PF_6$ in $DCM^a$ | $E_{1/2}^{+/0}$ vs. $Li^{+/0}$ (V) $LiPF_6$ in $EC/EMC^b$ | $LiBF_4$ in $PC^c$ | Diffusion Coefficient ($\times 10^{-6}$ $cm^2s^{-1}$) neutral, oxidized TBA-$PF_6$ in $DCM^d$ | $LiPF_6$ in $EC/EMC^e$ | $LiBF_4$ in $PC^f$ | Solubility 1.2M $LiPF_6$ in EC/EMC | 0.5M $LiBF_4$ in PC |
|---|---|---|---|---|---|---|---|---|---|---|
| EPT | 5.06 | N/A | 0.27 | 3.51 | 3.60 | 3.9, 2.4 | 1.0, 0.7 | 1.5, 1.4 | max. 0.1M | max. 0.1M |
| MEPT | 5.11 | 5.21 | 0.30 | 3.56 | 3.64 | 3.7, 2.6 | 0.4, 0.2 | 1.1, 1.0 | at least 50 wt. % | at least 50 wt. % |
| MEEPT | 5.12 | 5.21 | 0.29 | 3.60 | 3.64 | 2.5, 1.6 | 0.2, 0.1 | 0.7, 0.7 | at least 50 wt. % | at least 50 wt. % |

$^a$80 mM analyte in 100 mM TBA-$PF_6$/DCM recorded at 100 mV/s scan rate.
$^b$80 mM analyte in 1.2M $LiPF_6$ in EC/EMC (3:7 wt. ratio) at 100 mV/s scan rate
$^c$10 mM analyte in 0.5M $LiBF_4$/PC recorded at 100 mV/s scan rate.
$^d$10 mM analyte in 100 mM TBA-$PF_6$/DCM recorded at scan rates from 10 to 200 mV/s.
$^e$80 mM analyte in 1.2M $LiPF_6$ in EC/EMC (3:7 wt. ratio) at scan rates from 5 to 500 mV/s.
$^f$10 mM analyte in 0.5M $LiBF_4$/PC at scan rates from 5 to 500 mV/s.

TABLE 2

Energies of the highest-occupied molecular orbitals (HOMOs) for MEPT and MEEPT in the absence and presence of chelated $Li^+$ as determined at the B3LYP/6-311G(d, p) level of theory. The data tabulated under the 'solvent' column were computed using the SCRF polarizable continuum model with ε = 51.1 to account for the battery environment. All energies are reported in eV. The large deviation with regard to the HOMO energies of $Li^+$-MEPT vs $Li^+$-MEEPT for the isolated ('gas phase') molecules, which is not seen when the solvent dielectric is taken into account, arises from a considerable geometric distortion in $Li^+$-MEPT, FIG. 11. The lone oxygen atom in the methoxyethyl side chain is not able to bind $Li^+$ alone, and the phenothiazine moiety is required to stabilize the chelation. When the influence of the solvent is considered, the dielectric screening allows the $Li^+$ to be more readily bound to the oxygen atom in the methoxyethyl side chain, though not as strongly as with the methoxyethoxyethly group.

Figure 3:
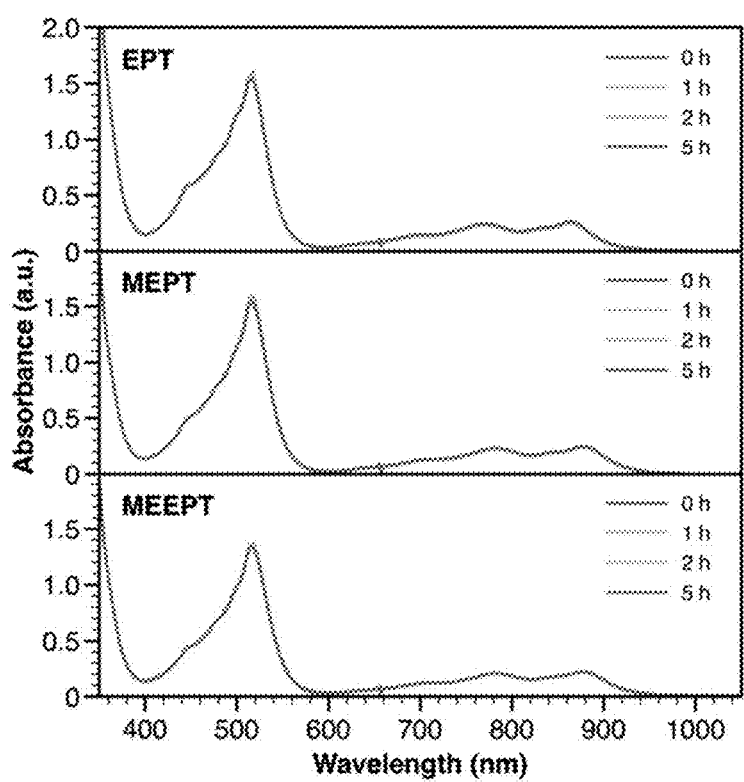
FIG. 3 shows UV-vis spectra of the radical cations of EPT (top), MEPT (middle), and MEEPT (bottom) at 0.167 mM in DCM 0 to 5 h after generation through chemical oxidation with $TBPA-SbCl_6$.

| | Isolated ('gas phase') | | Solvent | |
|---|---|---|---|---|
| | HOMO | Δ ($Li^+$-bound-free) | HOMO (eV) | Δ ($Li^+$-bound-free) |
| MEPT | −5.35 | 4.27 | −5.53 | 0.1 |
| $Li^+$-MEPT | −9.62 | | −5.63 | |
| MEEPT | −5.36 | 2.37 | −5.54 | 0.1 |
| $Li^+$-MEEPT | −7.73 | | −5.64 | | solutions were monitored (FIG. 3), suggesting that the radical cations are highly stable.

Figure 4:
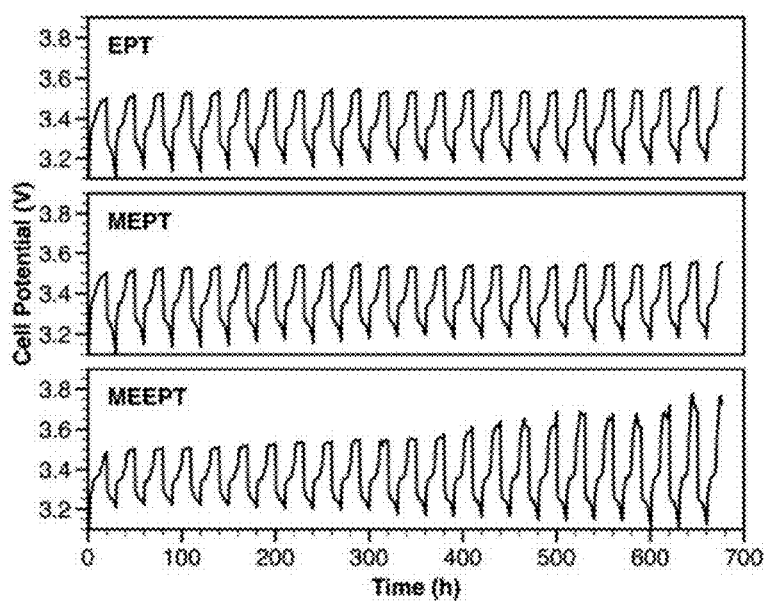
FIG. 4 shows overcharge cycling of LFP/graphite coin cells containing 80 mM EPT, MEPT, or MEEPT in Gen 2 electrolyte at 100% overcharge per cycle at C/10 rate (20 h charge, 10 h discharge).

To determine if the high stability of MEPT and MEEPT were compatible in high concentrations in the neutral and radical cation forms in an environment with greater similarities to that of a non-aqueous RFB, the performance of these electro-active species in overcharging LIBs was evaluated, a method that Zhang and coworkers have also used to analyze the stability of electro-active material candidates. Overcharge experiments with MEPT and MEEPT were conducted at both low (80 mM) and high (1.0 M) concentrations in Gen 2 battery electrolyte in coin cells containing $LiFePO_4$ (LFP) cathodes and graphitic anodes. At 80 mM, EPT, MEPT, and MEEPT were cycled at a rate of C/10 where the charge passed was double that needed to reach 100% state of charge (SOC), and then discharged at the same rate. As expected from the CV characterization, MEPT and MEEPT show higher shuttling potentials (3.50 and 3.55 V, respectively) than EPT (3.40 V) (FIG. 4). This difference is likely due to coordination of $Li^+$ to the redox shuttle, increasing the oxidation potentials. MEPT and MEEPT show comparable ability to shuttle charge at this concentration and rate to EPT; experiments reached over 700 h of 100% overcharge cycling are still in progress at the time of manuscript submission (FIG. 4).

Figure 5:
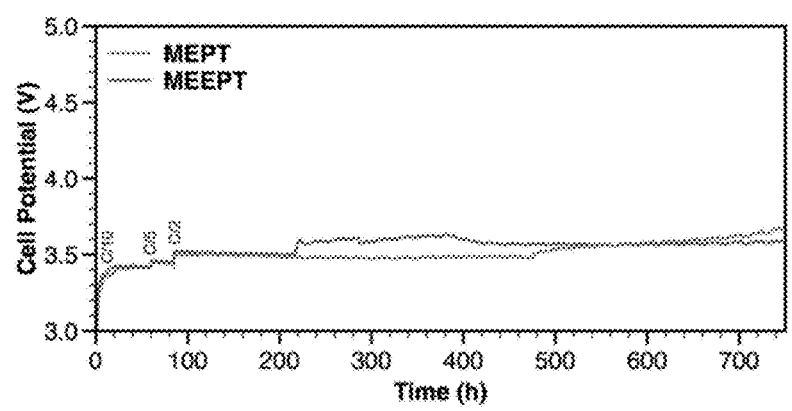
FIG. 5 shows constant overcharge in LFP/MAG10 coin cells with 1.0 M MEPT or MEEPT. Rates ramped from C/10 to C/2.

MEPT and MEEPT can be formulated with battery electrolyte at much higher concentrations than those needed for overcharge protection at the C/10 charging rate. To test performance at higher concentrations, LFP/MAG10 coin cells were prepared with 1.0 M redox shuttle in battery electrolyte and cycled using a no-discharge protocol at a charging rate of C/2. As shown in FIG. 5, at concentrations of 1.0 M, both shuttles prevent overcharge at C/2 for extended periods of time (over 700 h at time of manuscript submission).

Figure 6:
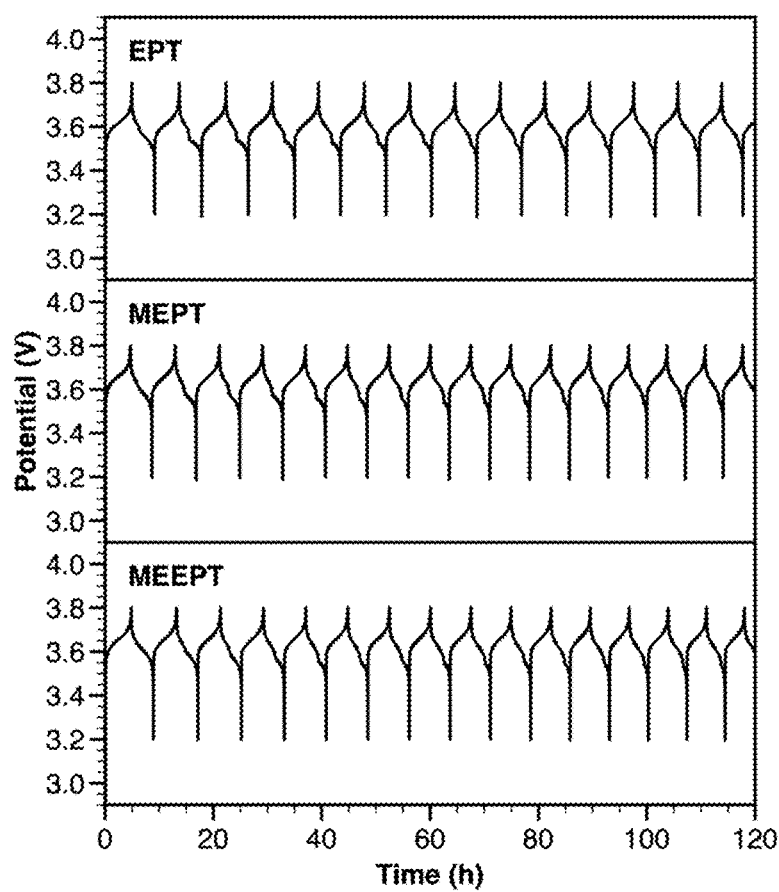
FIG. 6 shows charge-discharge profiles of EPT, MEPT and MEEPT at 10 mM in 0.5 M $LiBF_4$ in PC from 0-100% SOC at a rate of C/5 for 120 h in a coin cell with Li metal as the negative electrode.
Figure 10:
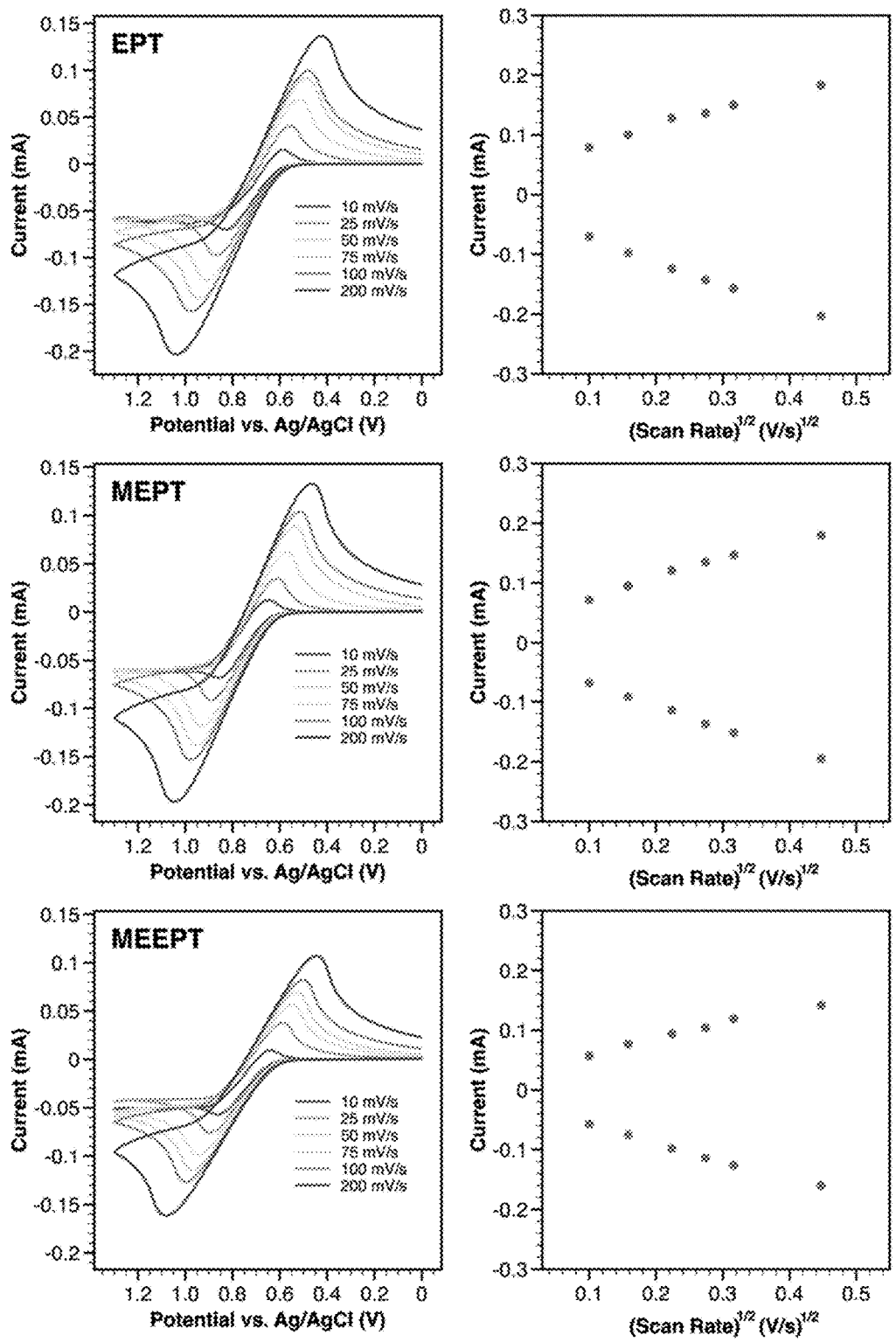
FIG. 10 shows cyclic voltammograms of EPT, MEPT, and MEEPT at 10 mM in 0.1 M $TBAPF_6$ in DCM recorded at scan rates from 10 to 200 mV/s. Plots of peak current vs. square root of scan rate of 10 mM EPT, MEPT and MEEPT in 0.1 M $TBAPF_6$ in DCM

Next, to evaluate MEPT and MEEPT as cathode candidates for RFBs, the performance of the redox-active species over multiple charge and discharge cycles was analyzed, albeit in a static environment, using galvanostatic cycling in MEPT/Li and MEEPT/Li coin cells. Here we employed the electrolyte 0.5 M $LiBF_4$ in PC in which both MEPT and MEEPT are miscible at as high as 50 wt. % (Table 1). The positive electrode was composed of graphite felt soaked in catholyte consisting of 10 mM active species in 0.5 M $LiBF_4$ in PC, and Li metal was employed as the negative electrode. The electrodes were separated by a lithiated Nafion membrane. The coin cells were cycled between 3.2 and 3.8 V at a rate of C/5 up to 100% SOC so that the first oxidation would be accessed. The theoretical capacities of EPT, MEPT, and MEEPT are 118 mAh/g, 104 mAh/g, and 89 mAh/g, respectively. The charge-discharge profiles for all three catholytes for 120 h are shown in FIG. 6. The charge and discharge plateaus occur in accordance with the potentials determined by CV; they represent the formation and reversible reduction of the respective radical cations. The capacity profiles (FIG. 10) indicate that each compound is able to reach the approximate theoretical capacity in the first cycle, following which the capacity slowly decreases with each cycle, suggesting a slow but continuous consumption of redox species by a side reaction. The gap between the charge and discharge capacities may result from crossover of the charged species. This is supported by the marginally smaller gap exhibited by cells containing MEEPT, which is slower to diffuse than EPT or MEPT (Table 1). EPT, MEPT, and MEEPT retained ca. 76%, 68% and 67%, respectively, of the original charge capacity after 30 cycles, over which time the coulombic efficiencies for all three catholytes stabilized at ca. 90%.

The two phenothiazine derivatives featuring oligoether substituents at the N position have been successfully synthesized and assessed within a battery system. These derivatives were found to be liquids at room temperature and fully miscible with battery electrolytes at high concentrations. Electrochemical measurements and DFT calculations suggest that these derivatives have oxidation potentials slightly higher than N-alkyl phenothiazine derivatives, posited to be due to lithium-complexation by the oligoether side-chain. At low concentration (80 mM), these derivatives show extended overcharge protection at C/10 charging rates. At high concentration (1 M), both compounds exhibit overcharge protection for extended overcharge protection at rates as high as C/2 for over 1000 h (in progress). These highly soluble compounds function as electron donors in static half-cells with Li metal, showing great promise for use in non-aqueous RFBs.

EXAMPLES

General.

Anhydrous dichloromethane (DCM, 99.9% purity), phenothiazine (99%), sodium hydride (60% dispersion in mineral oil) and lithium tetrafluoroborate (98%, anhydrous) were purchased from Acros Organics. 2-Chloroethyl methyl ether (98%) and 1-bromo-2-(2-methoxyetoxy)ethane (90%) were purchased from Alfa Aesar. Nafion 117 membrane and Li metal ribbon were purchased from Sigma Aldrich. Other reagents and chromatography solvents were purchased from VWR. TBPA-$SbCl_6$ (technical grade) was purchased from Sigma-Aldrich. Silica gel (65×250 mesh) was purchased from Sorbent Technologies. For electrochemical measurements, electrolyte salts and solvents (EC, EMC, PC, $LiPF_6$, $LiBF_4$) were battery grade, purchased from BASF Corporation (Florham Park, N.J.). $^1H$ and $^{13}C$ NMR spectra were obtained on Varian spectrometers in $CDCl_3$ from Cambridge Isotope Laboratories.

Synthesis.

Redox shuttles were synthesized by alkylation of phenothiazine with the corresponding alkyl halide. EPT was synthesized as previously described (Ergun et al., Chem. Commun., 2014, 50, 5339-5341). Phenothiazine (1.99 g, 10.0 mmol) was dissolved in DMF (20 mL). For new compounds MEPT and MEEPT dispersion of NaH in mineral oil (0.48 g, 12 mmol) was added and the reaction mixture was heated to 60° C. for 30 min. Then, 2-chloroethyl methyl ether (1.10 mL, 12 mmol, for MEPT) or 1-bromo-2-(2-methoxyetoxy)ethane (1.62 mL, 12 mmol, for MEEPT) was added, and the reaction was stirred at 60° C. for 12 h. The reaction was quenched by pouring it onto ice water, after which the organic components were extracted with ethyl acetate three times, and the combined extracts were washed with brine. The organic extracts were dried over $MgSO_4$, filtered to remove solids, and concentrated by rotary evaporation. The crude product was purified by column chromatography using a gradient of 0 to 10% ethyl acetate in hexanes to afford the desired products as colorless oils.

N-(2-methoxyethyl)phenothiazine (MEPT). Yield: 2.16 g (84%). $^1H$ NMR (400 MHz, $CDCl_3$): δ 3.38 (s, 3H), 3.74 (t, 2H, J=6.4 Hz), 4.07 (t, 2H, J=6.4 Hz), 6.87-6.92 (m, 4H), 7.10-7.24 (m, 4H). $^{13}C$ NMR (100 MHz, $CDCl_3$): δ 47.37, 59.09, 69.74, 115.17, 122.62, 124.67, 127.33, 127.45, 144.96. EI-MS: m/z 257 (54%), 212 (100%), 198 (20%), 180 (61%). Anal. calcd. for $C_{15}H_{15}NOS$ C, 70.01; H, 5.88; N, 5.44. Found C, 69.99; H, 5.91; N, 5.39.

N-[2-(2-methoxyethoxy)ethyl]phenothiazine (MEEPT). Yield: 2.22 g (74%). $^1$H NMR (400 MHz, CDCl$_3$): δ 3.34 (s, 3H), 3.51-3.54 (m, 2H), 3.61-3.64 (m, 2H), 3.83 (t, 2H, 1=6.4 Hz), 4.10 (t, 2H, 1=6.4 Hz), 6.87-6.92 (m, 4H), 7.10-7.24 (m, 4H). $^{13}$C NMR (100 MHz, CDCl$_3$): δ 47.37, 59.09, 69.74, 115.17, 122.63, 124.67, 127.33, 127.45, 144.96. EI-MS: m/z 301 (48%), 212 (100%), 198 (22%), 180 (46%). Anal. calcd. for $C_{17}H_{19}NO_2S$ C, 67.75; H, 6.35; N, 4.65. Found C, 67.48; H, 6.41; N, 4.88.

Another identified branched phenothiazine (Branch PT) was: produced from a first step:

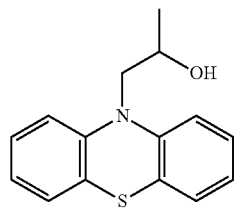

isolated by $^1$HNMR (400 MHz, CDCl3): δ=1.29 (d, J=6.4 Hz, 3H), 2.40 (br.s, 1H), 3.79 (dd, J=13.6, 9.2 Hz, 1H), 3.99 (dd, J=13.2, 3.2 Hz, 1H), 4.18-4.21 (m, 1H), 6.92-6.99 (m, 4H), 7.16-7.26 (m, 4H). GCMS: m/z 285 ( ), 212 ( ), 198 ( ), 180 ( ). This was followed by a second step to produce

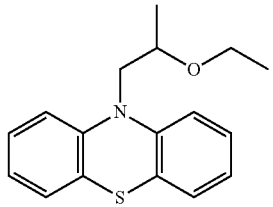 [SMILES: CCOC(C)CN1c2ccccc2Sc2ccccc21]

isolated by $^1$HNMR (400 MHz, DMSO): δ=1.00 (t, J=7.2 Hz, 3H), 1.13 (d, J=6 Hz, 3H), 3.45 (q, 6.8 Hz, 2H), 3.71-3.80 (m, 2H), 3.98-4.03 (m, 1H), 6.95 (dt, J=8 Hz, 2H), 7.08 (d, 8 Hz, 2H), 7.15-7.22 (m, 4H). GCMS: m/z 257 ( ), 212 ( ), 198 ( ), 180 ( )

Electrochemical Analysis.

Cyclic voltammetry (CV) experiments were performed using a CH Instruments 600D potentiostat using a three-electrode system in either 100 mM TBAPF$_6$ in anhydrous DCM or in 1.2 M LiPF$_6$ in ethylene carbonate (EC)/ethyl methyl carbonate (EMC) (3:7 wt. ratio) containing 0.8 mM redox shuttle. Cyclic voltammograms were also recorded in 0.5 M LiBF$_4$ in propylene carbonate (PC) containing 10 mM analyte. Glassy carbon was used as the working electrode, platinum wire as the counter electrode and either freshly anodized Ag/AgCl (in DCM) or lithium metal (in battery electrolyte) as reference electrodes. Oxidation potentials are reported relative to ferrocenium/ferrocene ($Cp_2Fe^{+/0}$) in DCM or to $Li^{+/0}$ in battery electrolyte. Voltammograms were recorded at a scan rate of 100 mV/s. To determine diffusion coefficients, voltammograms were recorded at variable rates between 5 and 500 mV/s at analyte concentration of 80 mM in 1.2 M LiPF$_6$ in EC/EMC and 10 mM in 0.5 M LiBF$_4$ in PC.

Radical Cation Stability.

UV-vis spectra were collected using optical glass cuvettes (Starna) with 1 cm path length with an Agilent 8453 diode array spectrometer. Radical cations were generated in anhydrous DCM by the addition of a 1 mL DCM solution of 0.50 mM TBPA-SbCl$_6$ to a 2 mL DCM solution containing 2.5 mM analyte to produce a final solution containing 0.17 mM radical cation with 1.7 mM analyte, which generates 0.17 mM analyte radical cation with a 9-fold excess of neutral analyte. The cuvettes were capped, and spectra were collected for 5 h.

Battery Cycling.

Overcharge tests were conducted with stainless steel 2032 coin cells using LiFePO$_4$ (MTI, Richmond, Calif.) as the cathode and MAG-10 (APHEVB, Argonne National Laboratory) as the anode. The anode was composed of 95 wt. % MAG-10 graphite (Hitachi) as the active material and 5 wt. % SBR/CMC (50/50) as the binder. The electrolyte used in coin cell testing was 1.2 M LiPF$_6$ in EC/EMC (3:7 wt. %). Microporous PP/PE/PP trilayer separators from Celgard were used to prevent contact between the anode and cathode. Coin cells were prepared in an argon-filled glovebox with <0.1 ppm oxygen or water present. A Landt CT2001A battery cycler was used for coin cell cycling. Overcharge cycling was conducted by charging with constant current at rate of C/10 for 20 h, followed by discharge at a rate of C/10 for 10 h. This process was repeated until cell potential reached 5 V. Constant current experiments were conducted by programming to constantly charge a coin cell by applying charging currents corresponding to rates of C/10 for 60 h, C/5 for 25 h and C/2 until the cell potential reaches 5 V.

Static Coin Cell Cycling.

The charge/discharge experiments were performed using a coin cell cycled by a Landt CT2001A battery cycler. All solutions were prepared in the argon-filled glovebox at room temperature. The catholyte used contained 10 mM EPT, MEPT, or MEEPT in 0.5 M LiBF$_4$ in PC. Nafion 117 was used as the separator membrane between a graphite felt electrode (Sigracell® GFD3) and Li metal electrode. The graphite felt was vacuum dried at 80° C. overnight prior to use. The positive graphite electrodes were soaked in solutions of respective catholytes, for 3-4 h prior to use. When soaked, the foam electrodes absorb approximately 0.43 g of solution (active material: 0.7-1.0 mg). The Nafion membrane was pretreated and soaked in a solution of 0.5 M LiBF$_4$ in PC for 3-4 h prior to use. Each coin cell was assembled in the glovebox and was removed for cycling. The cells were cycled between 3.2 and 3.8 V at a constant current of ca. 0.02 mA, corresponding to C/5 current rate. The charge process continued until the cell reach 100% theoretical capacity or 3.8 V voltage limit, whichever occurred first. Similarly, the discharge process was controlled by reaching 100% theoretical capacity or voltage limit of 3.2 V.

In summary, phenothiazine derivatives featuring oligoether substituents at the N position were synthesized. These derivatives were found to be liquids at room temperature and fully miscible with battery electrolytes at high concentrations. Electrochemical measurements and DFT calculations suggest that these derivatives have oxidation potentials slightly higher than N-alkyl phenothiazine derivatives, posited to be due to lithium-complexation by the oligoether side-chain. At low concentration (80 mM), these derivatives show extended overcharge protection at C/10 charging rates. At high concentration (1 M), both compounds exhibit overcharge protection for extended overcharge protection at rates as high as C/2 for over 1000 h (in progress). These highly soluble compounds function as electron donors in static half-cells with Li metal, showing great promise for use in non-aqueous RFBs.

The foregoing has been presented for purposes of illustration and description. It is not intended to be exhaustive or to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled. All referenced cited herein are hereby incorporated by referenced in their entirety.

The invention claimed is:

1. A composition for a catholyte solution comprising a lithium-containing organic solvent and a phenothiazine derivative with a substituent at the N position, wherein the substituent is an oligoglycol chain, and wherein the phenothiazine derivative is not further substituted by a perfluoroalkyl group.

2. The composition of claim 1, wherein the oligoglycol chain is branched.

3. The composition of claim 1, wherein the oligoglycol chain is linear.

4. The composition of claim 1, further comprising at least a second substituent at the 1, 2, 3, 4, 6, 7, 8 and/or 9 positions, wherein the second substituent is selected from the group consisting of a halogen, an alkoxy group, a carbonyl group, a nitrile group, a nitro group, an alkyl, or combinations thereof.

5. A flow battery comprising a positive electrode resting in the catholyte solution of claim 1 and a negative electrode, wherein the negative electrode and the positive electrode are separated by a membrane.

* * * * *